(12) United States Patent
Birkel et al.

(10) Patent No.: US 6,358,493 B1
(45) Date of Patent: Mar. 19, 2002

US006358493B1

(54) METHODS OF PERFORMING COSMETIC TREATMENTS WITH GASIFIED SOLID PARTICLES AND INSTANT GEL PREPARATIONS CONTAINING THE GASIFIED SOLID PARTICLES

(75) Inventors: Susanne Birkel, Rossdorf; Harald Wendel; Karin Steinbrecht, both of Ober-Ramstadt; Wolfgang Maurer, Schriesheim, all of (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/590,649

(22) Filed: Jun. 8, 2000

(30) Foreign Application Priority Data

| Jun. 9, 1999 | (DE) | 199 26 316 |
| Apr. 19, 2000 | (DE) | 100 19 313 |

(51) Int. Cl.$^7$ ............ A01N 25/02; A01N 59/04; A01N 43/04; A61K 9/00; A61K 6/00; A61K 7/00; A61K 9/16; A61K 9/50; A61K 7/06; A61K 7/11; A61K 33/00; A61K 31/90; A61L 9/04

(52) U.S. Cl. ............ 424/43; 424/401; 424/493; 424/70.1; 424/70.11; 424/700; 514/24; 514/881; 514/944

(58) Field of Search ............ 424/401, 493, 424/494, 43, 47, 70.1, 70.11, 700; 514/24, 881, 944

(56) References Cited

U.S. PATENT DOCUMENTS

| 3,012,893 | A |   | 12/1961 | Kremzner |
| 3,947,566 | A |   | 3/1976 | Sarna et al. |
| 3,947,567 | A | * | 3/1976 | Berg et al. ............ 424/45 |
| 3,947,568 | A | * | 3/1976 | Bates et al. ............ 424/47 |
| 4,262,029 | A |   | 4/1981 | Kleiner et al. |
| 4,275,083 | A |   | 6/1981 | Colten et al. |
| 4,592,855 | A | * | 6/1986 | Gioffre et al. ............ 252/89.1 |
| 4,627,972 | A |   | 12/1986 | Gioffre et al. |
| 4,818,518 | A |   | 4/1989 | Gioffre et al. |
| 5,824,629 | A | * | 10/1998 | Petritsch ............ 510/120 |
| 5,993,854 | A | * | 11/1999 | Needleman et al. ............ 424/466 |

FOREIGN PATENT DOCUMENTS

| DE | 197 45 964 A1 | 6/1998 |
| EP | 0 017 691 A1 | 10/1980 |
| EP | 0 201 589 | 6/1986 |
| EP | 0 326 692 A2 | 8/1989 |
| EP | 0 533 609 A1 | 3/1993 |
| EP | 0 312 952 B1 | 1/1994 |
| EP | 0 441 507 B1 | 3/1996 |
| WO | 86/01376 | 3/1986 |

OTHER PUBLICATIONS

Translation of DE 19745964, Kripp et al., published 6/98.*
Zeitschrift fuer die Chemisch–Technische Industrie, die Technische Chemie und Spezialchemikalien, "Mikroverkapselung" by Bruno Hertrich, Seifen–Oele–Fette–Wachse–115. JG, NR. Mar. 1989, pp. 93–98.

* cited by examiner

*Primary Examiner*—Dameron L. Jones
*Assistant Examiner*—Lauren Q. Wells
(74) *Attorney, Agent, or Firm*—Michael J. Striker

(57) ABSTRACT

Gasified particles for cosmetic treatments, particularly hair treatments, are described. The gasified particles contain at least one gas enclosed in a solid enveloping material. The enveloping material is selected so that the gas is released on contact of the enveloping material with water or moisture. The release of the gas can be accompanied by a detectable acoustic effect (pop effect). The hair treatment composition also can provide a hair fixing effect. Furthermore an instant gel preparation is described substantially comprising a mixture of dry substances, which contains at least one gel former and at least one solid substance producing a detectable acoustic effect on contact with moisture, especially gasified particles. The gasified particles are used as acoustic indicators for the readiness of the instant preparation after liquid addition.

24 Claims, No Drawings

METHODS OF PERFORMING COSMETIC TREATMENTS WITH GASIFIED SOLID PARTICLES AND INSTANT GEL PREPARATIONS CONTAINING THE GASIFIED SOLID PARTICLES

BACKGROUND OF THE INVENTION

The subject matter of the present invention is the use of gasified particles for cosmetic treatments, especially for treating hair, in which the gasified particles contain at least one gas enclosed in a suitable enveloping material. The gas is released on contact of the enveloping material with moisture or water. The release of the gas can be accompanied by a special sensory, especially tactile or acoustic effect (pop effect). The subject matter of the present invention also includes an instant gel preparation made from a mixture of solid gel formers and a solid material producing an observable effect when contacted by moisture and a suitable cosmetic agent. In addition, the subject matter of the invention includes a method of using gasified particles as acoustic indicators for signaling the readiness of an instant preparation after addition to a liquid.

SUMMARY OF THE INVENTION

The basic purpose of the invention is to provide cosmetic compositions with new properties. One such property, for example, is a sensory effect, especially a tactile or acoustic effect, produced during use of the cosmetic composition. The conventional cosmetic action generally should not be impaired by these new properties, but ideally even improved because of them.

The instant preparations are characterized in that they contain solid, mostly powdery or granular materials, which when added to a liquid, especially water, dissolve with gentle stirring and produce a ready-to-use mixture. The consistence of the ready-to-use mixture for optimum application is reached so that it is not always easy for the user to detect the time point at which the desired consistency is reached.

These popping candies are described in various patent applications and patents including U.S. Pat. Nos. 3,012,893, 4,262,029, 4,275,083, EP 0 017 691, EP 0 326 692, EP 0 533 609 and WP 86/01376 as well as the references cited in the foregoing patents and patent applications. A description of the mechanism forming the basis for this pop effect and the parameters, which determine the extent, quality and time delay for the pop effect, are disclosed in EP 0 533 609. In the manufacture of popping candy usually sugar is melted and a gas, preferably carbon dioxide, is dispersed in the melt. When the melt has cooled, the sugar solidifies, the dispersed gas is enclosed and forms a solid foam. Granulates can be made, which contain gas bubbles in an envelope of solid sugar and in which the gas pressure in the bubbles is greater than the surrounding pressure. The gas can also be worked into the candy material under pressure in an autoclave. The solid enveloping material dissolves on contact with moisture until the stability of the envelope is reduced until it is overcome, or the surface tension is reduced until it is less than the force produced by the internal pressure. Then the enveloping material bursts and the gas escapes producing an observable acoustic or tactile effect.

It has been found that systems of this type can also be used in cosmetic applications, especially for hair treatment. The subject matter of the invention is thus the use of gasified particles, which contain at least one gas enclosed in a solid enveloping material. The enveloping material is selected so that the gas is released on contact of it with water or moisture during cosmetic treatments, especially treatment of hair. The subject matter of the invention thus includes a cosmetic composition with a content of at least one gas enclosed in a solid enveloping material or matrix. The solid material or matrix is selected so that the gas is released on contact with water or moisture.

The enclosed gas may be an inert gas or an appropriate gas mixture, and is preferably carbon dioxide, oxygen, nitrogen or air, of which carbon dioxide is especially preferred, since it provides an intense sound effect.

The enveloping material is preferably based on sugar, i.e. based on mono-, oligo- or polysaccharides. The sugar particularly can be sucrose, lactose, glucose, dextrose, maltose, fructose, disaccharides, trisaccharides, tetrasaccharides, pentasaccharides, hexasaccharides and higher oligo- or polysaccharides or sugar materials, such as sorbitol or their mixtures. The gas release is delayed when sorbitol or mixtures of it are used, because it dissolves more slowly in water. A delayed gas release or an extension of the effect connected with it can thus be achieved, since the gasified particles are combined with an aqueous, highly viscous, especially gel-form, preparation, with which they are mixed or contacted immediately prior to application. Preferably a mixture of different sugars, e.g. a mixture of sucrose, lactose and glucose, is used. The content of enclosed gas preferably amounts to from 0.05 to 15, especially preferably from 0.3 to 2.0 $cm^3$ per gram of total mass. The particle size amounts to preferably from 0.1 to 5 mm, especially preferably from 0.5 to 4.5 mm. The particles can be coated with a suitable material, e.g. with fats, shellac, gelatin or cellulose derivative compounds, such as hydroxyalkylcellulose, especially hydroxymethylcellulose, hydroxyethylcellulose or hydroxypropylcellulose. The coating material is preferably hydrophobic. The preparation of suitable granulates containing gases enclosed in a sugar envelope or matrix is disclosed in U.S. Pat. Nos. 3,012,893, 4,262,029, EP 0 533 609, EP 0 017 691 and the literature cited in those references. Suitable granulates are obtainable commercially, for example the popping candy of Zeta, Espacial S. A., Rubi, Spain. The manufacture of coated gasified particles is described in U.S. Pat. No. 4,275,083.

Cosmetic compositions according to the invention preferably comprise two components separate from each other prior to application. A first component contains at least one cosmetic effective ingredient in an aqueous cosmetic base and can be a conventional cosmetic preparation, e.g. a shampoo, a hair care composition, a hair styling gel or a hair styling foam. The second component comprises or contains particles, which contain at least one gas in a solid envelope. The two components can be either packaged in a two-component package, e.g. a commercial two-compartment package or in a set comprising two separate packages.

The cosmetic composition according to the invention contains preferably from 1 to 75, especially preferably from 3 to 30, percent by weight of the gasified particles. In principle the gasified particles can be used in combination with any arbitrarily selected cosmetic agent with an aqueous base to provide a sensory, especially acoustic and/or tactile, effect. The cosmetic agent can be present in the form of a hair or body cleansing agent, a hair care agent, a hair fixing agent, a hair dyeing or tinting agent, a bleaching agent or a permanent wave agent. The cosmetic composition can be applied in the form of a lotion, a foam, a milk, a gel, a cream or gel foam or in the form of an emulsion-forming hair care agent (hair rinse, conditioner).

The sugar matrix or enveloping material is dissolved on contact with water or moisture and the gas enclosed is released. For example, this is the case when the aqueous cosmetic preparation such as a shampoo, a care composition, a styling gel or a styling foam, comes into contact with moist hair. Because the sugar enveloping material has a high affinity for hair, after a suitable hair treatment and after washing the shampoo or care composition out, the treated hair has a positive volumetric effect.

The composition according to the invention can also be in the form of a substantially water-free single component composition. If present in the form of a dry shampoo, it also contains a water-active surfactant or surfactant mixture.

The composition according to the invention can contain conventional additive ingredients suitable for hair treatment compositions. These conventional additive ingredients include, for example, solvents, such as water and lower aliphatic alcohols, for example ethanol, propanol and isopropanol, or glycols, such as glycerol and 1,2-propylene glycol; wetting agents or emulsifiers from the classes of anionic, cationic, amphoteric or nonionogenic surface-active substances, such as fatty alcohol sulfates, alkylbenzene sulfonates, alkyltrimethylammonium salts, moisturizers, alkyl betaines, ethoxylated fatty alcohols, ethoxylated nonylphenols, fatty acid alkanol amides, ethoxylated fatty acid esters, in an amount of from 0.1 to 30 percent by weight, perfume oils, in an amount of from 0.1 to 0.5% by weight; turbidity-inducing agents, such as ethylene glycol distearate, in an amount of about 0.2 to 5.0 percent by weight; pearlescence-imparting agents, such as a mixture of fatty acid monoalkylamides and ethylene glycol distearate, in an amount of about 1.0 to 10 percent by weight; bactericides and fungicides, such as 2,4,4-tricholoro-2-hydroxydiphenyl ether or methylchloroisothiazolion, in an amount of from 0.01 to 1.0% by weight; thickeners, such as coconut fatty acid diethanolamide, in an amount of about 0.2 to 3.0 percent by weight; buffer substances, such as sodium citrate or sodium phosphate, in an amount of from 0.1 to 1.0 percent by weight; solvating agents, such as ethoxylated castor oil, in an amount of about 0.1 to 1.0 percent by weight; dyeing materials, such as fluorescein sodium salt, in an amount of about 0.1 to 1.0 percent by weight; care substances, such as plant and herbal extracts, proteins and silk hydrolyzates, cationic resins, lanolin derivatives, in an amount of from 0.1 to 5 percent by weight; physiologically compatible silicone derivative compounds, such as silicone oil, silicone polymers and siloxanes; light-protective agents, antioxidants, radical trapping agents, anti-flaking substances, in amounts of about 0.01 to 2 percent by weight; physiologically compatible organic acids, such as formic acid, glyoxylic acid, lactic acid, tartaric acid, citric acid, natural, modified natural or synthetic polymers, such as shellac, cationic, anionic, nonionic, amphoteric polymers, hydroxycellulose, chitosan, chitin or chitosan derivative compounds; direct-dyeing hair dye materials, hair dye substances, which are developed oxidatively, oxidation agents, reduction agents, fatty alcohols, luster-imparting agents, vitamins, softeners and combability improving substances, defatting agents, foam-breaking substances and propellants, such as fluorohydrocarbons, dimethyl ether, hydrocarbons and compressed gases.

When the composition according to the invention is present as a hair and/or body cleansing composition, for example as a shampoo or douche gel, it contains at least one wash-active surfactant or surfactant mixture.

Suitable anionic surfactants include, e.g. alkyl sulfates, alkyl ether sulfates, alpha-olefin sulfonates, sulfosuccinates, such as disodium laureth-3 sulfosuccinate, disodium PEG-5 lauryl citrate sulfosuccinate, disodium ricinolamido MEA-sulfosuccinate or disodium laurylamido MEA-sulfosuccinate and ether carboxylates, such as sodium laureth-6 carboxylate or sodium laureth-11 carboxylate.

Suitable nonionic surfactants include e.g. alkoxylated fatty alcohols with a high degree of alkoxylation, e.g. from 11 to 50 and alkoxylated fatty acid esters, alkoxylated partial glycerides of branched or unbranched, saturated or unsaturated $C_6$- to $C_{20}$-fatty acids, and with an alkoxylation degree of 11 to 400, e.g. polyethylene glycol (200) glyceryl palmitate, alkoxylated polyol esters, such as ethoxylated sugar esters, for example polyethylene glycol(120)methyl glucose dioleate and alkylpolyglucosides, such as coconut glucosides, lauryl gluycosides or decylglucosides. For example, ethoxylate lauryl-, tetradecyl-, cetyl-, oleyl- or stearyl alcohol, which are used alone or in mixtures with each other, as well as fatty alcohols of ethoxylated lanolin, or ethoxylated lanolin, are suitable as fatty alcohol ethoxylates. Also ethoxylated fatty alcohols, which are marketed under the type name Dehydol® by Henkel or under the type name Brij® of ICI surfactants, are suitable for the hair treatment compositions according to the invention, in so far as they have a sufficiently high degree of ethoxylation.

Examples of the fatty acid ester ethoxylates include, above all, diglyceride ethoxylates and ethoxylated castor oils, such as PEG-25 hydrogenated castor oil, PEG-35 castor oil and PEG-40 hydrogenated castor oil.

Furthermore the ethoxylated fatty acid sugar esters known as nonionic surfactants, especially ethoxylated sorbitan fatty acid ester, but not ethyoxylated surfactants in general, are suitable for use in the cosmetic preparations according to the invention. The suitable ethoxylated fatty acid sugar esters include those marketed under the trade names Tween® and Arlacel® by ICI surfactants and the alkylpolyglycosides, which are marketed under the trade neames Plantaren® or Plantacare® by Henkel or under the trade name Oramix® by Seppic.

Suitable amphoteric surfactants include for example betaines, such as cocamidopropylbetaine or lauryl betaine, sulfobetaines, such as cocamidopropyl hydroxysultaine, glycinates, such as cocoamphoglycinate (INCI-name: sodium cocoamphoacetate) and -diglycinate and propionates, such as cocoampho-propionate.

When the composition according to the invention is a styling agent for hair, it also contains preferably at least one film-forming and hair-fixing polymer. The film-forming polymers are present in amounts of from 0.01 to 25, especially preferably from 0.1 to 20, percent by weight and can be used individually or in a mixture and in dissolved form or as a dispersion. The term "film-forming and hair-fixing polymer" means in connection with the present invention those polymers, which are in a position to deposit a polymer film on the hair and in this manner to fix the hair. The film-forming polymers can be nonionic, cationic, zwiterionic or amphoteric and can be of synthetic or natural origin. This sort of composition using fixing polymer in combination with gasified, sugar-coated or sugar-enveloped particles can be used as a hair fixing composition.

Suitable anionic hair-fixing polymers include synthetic homo- or copolymers with neutralizable monomer units containing acid groups, which are copolymerizable with comonomers, if necessary, which contain no acid groups. The acid groups may include sulfonic acid groups, phosphoric acid groups and carboxylic acid groups. Monomers containing suitable acid groups include, for example, acrylic acid, methacrylic acid, crotonic acid, maleic acid or maleic acid anhydride, aldehydocarboxylic acids or ketocarboxylic acids.

The comonomers not substituted with acid groups include, e.g., acryl amide, methacrylamides, alkyl and dialkylacrylamides, alkyl and dialkylmethacrylamides, alkylacrylates, alkylmethacrylates, vinylcaprolactone, vinylpyrrolidone, vinyl esters, vinyl alcohol, propylene glycol or ethylene glycol, amine-substituted vinyl monomers, such as dialkylaminoalkylacrylates, dialkylaminoalkylmethacrylates, monoalkylaminoalkylacrylates and monoalkylaminoalkylmethacrylates, in which the alkyl groups of these monomers preferably contain one to seven carbon atoms, especially preferably from one to three carbon atoms.

Suitable anionic polymers include homopolymers of acrylic acid or methacrylic acid that are uncross-linked or cross-linked with polyfunctional agents, copolymers of acrylic acid or methacrylic acid with monomers selected from the group consisting of acrylic acid or methacrylic acid esters, acryl amides, methacrylamides and vinylpyrrolidones, homopolymers of crotonic acid and copolymers of crotonic acid with monomers selected from the group consisting of vinyl esters, acrylic acid or methacrylic acid esters, acrylamides and methacrylamides. A suitable natural polymer is, for example, shellac.

Preferred polymers with acid groups include cross-linked or uncross-linked vinyl acetate/crotonic acid copolymers, which, for example, are sold in the form of a 60% solution in isopropanol/water under the trademark ARISTOFLE® of HOECHST, Germany or under the trademark LUVISET® CA-66 of BASF, Germany. Other suitable anionic polymers include, for example, terpolymers of vinyl acetate, crotonic acid and polyethylene oxide as well as terpolymers of acrylic acid, alkyl acrylate and N-alkylacrylamide, especially acrylic acid/ethyl acrylate/N-t-butylacrylamide terpolymer, as marketed under the trademark ULTRAHOLD® 8 and ULTRAHOLD® STRONG of BASF, Germany or terpolymers of vinyl acetate, crotonate and vinyl alkanoate, especially vinyl acetate/crotonate/vinyl neodecanoate copolymers, as sold under the trade name REYSN 28-2930 of National Starch.

Anionic polyurethanes are an additional class of suitable anionic polymers. Preferred polyurethanes are characterized as those (a) having terminal acid groups, which for example are introduced by means of aminosulfonic acids or aminocarboxylic acids, (b) if necessary containing additional free carboxylic acid groups, which are introduced by polymerizing in carboxylic acid diols, such as dimethylolpropanoic acid, as comonomers, and (c) containing polyurethane sequences, such as alkylene diisocyanates or isophorone diisocyanates. Luviset® PUR of BASF, Germany, is suitable for example.

The anionic polymers used in the composition according to the invention are partially or completely neutralized with a cosmetically compatible neutralizing agent. Organic or inorganic bases can be used as the neutralizing agent. For example especially aminoalkanols, such as aminomethylpropanol (AMP), tirethanolamines or monoethanolamines, also ammonia, NaOH, among others, are especially suitable for use as the base.

Suitable synthetic, nonionic, film-forming hair-fixing polymers include homo- or copolymers, which are built up from at least one nonionic monomer. Suitable nonionic monomers include, for example, acryl amides, methacryl amides, alkyl- and dialkylacrylamides, alkyl- and dialkylmethacrylamides, alkylacrylates, alkylmethacrylates, vinyl caprolactone, vinyl pyrrolidone, vinyl ester, vinyl alcohol, propylene glycol or ethylene glycol, wherein the alkyl groups of these monomers preferably have from one to seven carbon atoms, especially preferably from one to three carbon atoms. Suitable synthetic nonionic polymers include, for example, homopolymers of vinyl pyrrolidone and homopolymers of N-vinyl-formamide. Additional suitable synthetic film-forming nonionic hair-fixing polymers include, for example, the copolymerizates of vinyl pyrrolidone and vinyl acetate, terpolymers made from vinyl pyrrolidone, vinyl acetate and vinyl propionate, polyacrylamides, polyvinylalcohols, polyethylene glycols with a molecular weight of from 800 to 20,000 g/mol.

Suitable natural film-forming polymers include for example chitosan with a molecular weight of 20,000 to about 5 million g/mol, for example as marketed by Pronova, or different types of saccharides, for example polysaccharides or mixtures of oligo-, mono- and disaccharides, which are marketed under the trade name C-PUR® by Cerestar, Brussels, Belgium. Additional suitable natural polymers include Chinese pine resin and cellulose derivative compounds, for example hydroxypropyl cellulose with a molecular weight of from 30,000 to 50,000 g/mol.

Suitable cationic hair-fixing polymers are characterized by at least one type of monomer which contains cationic or cationizable groups, preferably primary, secondary, tertiary or quaternary nitrogen groups. Suitable ammonium-substituted vinyl monomers are, for example, trialkylmethacryloxyalkyl ammonium, trialkylacryloxyalkyl ammonium, dialkyldiallyammonium and quaternary ammonium vinyl monomer groups with cyclic, cationic nitrogen-containing groups, such as pyridinium, imidazolium or quaternary pyrrolidone groups, e.g. alkylvinylimidizolium which can be substituted on the heterocyclic ring with up to 3 $C_1$- to $C_{12}$-alkyl groups, alkylvinylpyridinium or alkylvinyl-pyrrolidone salts. Suitable amine-substituted vinyl monomers include, for example, dialkylaminoalkylacrylates, dialkylaminoalkylmethacrylates, monoalkylaminoalkylarylates and monoalkyl-aminoalkylmethacrylates, N-vinylimidzole, which can be substituted with up to 3 $C_1$- to $C_{12}$-alkyl groups on the ring. The alkyl groups of these monomers are preferably lower alkyl groups with from one to seven carbon atoms, especially one to three carbon atoms. The cationic or basic monomers can be copolymerized with nonionic or non-basic comonomers.

Suitable cationic polymers include, for example, polyvinylpyrrolidone/dimethylaminoethylmethacrylate copolymers, a copolymer of vinyl pyrrolidone with vinylimidazolium methochloride, a terpolymer of dimethyldiallylammonium chloride, sodium acrylate and acrylamide, a terpolymer of vinyl pyrrolidone, dimethylaminoethylmethacrylates and vinylcaprolactam, hydroxyethylcellulose substituted with quaternary ammonium groups, vinyl pyrrolidonel methacryl-amidodpropyltrimethylammonium chloride copolymer or diquaternary polydimethylsiloxane (INCI: Quaternium-80).

Suitable amphoteric polymers are those which contain both cationic or groups catonizable by protonation and also anionic or groups anionizable by deprotonation. Cationic groups are, for example, quaternary amino groups, cationizable groups are, for example, primary, secondary or tertiary amine groups. Anionic groups include, for example, carboxylate, sulfate, phosphate or phosphonate groups. Anionizable groups include, for example, the protonated forms of the named anionic groups.

Suitable amphoteric polymers are, for example, copolymers made from octylacrylamide, t-butylaminoethylmethacrylate and two or more monomers, comprising acrylic acid, methacrylic acid or their esters. At least one type of monomer contains an acid group. Further examples include copolymers of acrylic acid, methacrylate and methacrylamidopropyltrimethylammonium chloride (INCI: polyquaternium-47), copolymers made from acrylamidopropyltrimonium chloride and acrylates or copolymers made from acrylamide, acryl-amidopropyltrimonium chloride, 2-amidopropylacrylamide sulfonate and DMAPA (INCI: Polyquaternium-43).

When the hair treatment composition according to the invention is present in the form of a hair gel, it also contains at least one gel-former or gel-forming substance, for example a thickening agent selected from the group consisting of cross-linked or uncross-linked homopolymers of acrylic acid, especially carbopols, acrylic acid/acrylamide copolymers and natural thickeners, such as xanthan gum, cellulose derivative compounds. The thickeners are present in the compositions of the invention in amounts of preferably from 0.05 to 10, especially of 0.1 to 2, percent by weight. The viscosity of the gel amounts to preferably from 500 to 50,000 cSt, especially preferably from 1000 to 15,000 cSt at 25° (measured with a rotary viscometer according to DIN 53 018 T1 u. 2).

When the hair treatment agent according to the invention is present as a hair lotion, it is present as a flowing substantially non-viscose or slightly viscose solution, dispersion or emulsion with a content of at least 10, preferably from 20 to 95, percent by weight of a cosmetically compatible alcohol. Lower alcohols with one to four carbon atoms, such as ethanol or isopropanol, are used as the alcohols suitable for cosmetic purposes.

The composition according to the invention is used in the form of a hair dyeing or tinting composition, it also contains from 0.05 to 2.0 percent by weight of at least one direct-dyeing hair dyestuff, which is selected from the following classes of hair dye compounds for direct dyeing of hair: aromatic nitro dye compounds, for example 1,4-diamino-2-nitrobenzene; azo dye compounds, for example Acid Brown 4 (C.I. 14 805); anthraquinone dye compounds, for example Disperse Violet 4 (C.I. 61 105), triphenylmethandye compounds, for example Basic Violet 1 (C.I. 42 535). These dye compounds can have acidic, nonionic or basic character according to the nature of their substituents. The direct-dyeing hair dyestuffs can also include those natural dyestuffs, such as Henna or Reng, which do not required oxidation to develop color.

The compositions of the invention can be used to treat hair by a method in which an aqueous hair treatment composition is mixed with particles which contain at least one gas enclosed in a solid water-soluble enveloping material in a first step and the mixture is applied in a second step subsequently directly to the hair. In another embodiment of the method in a first step the hair is washed, rinsed or otherwise moistened with water and in a second step a water-free composition is applied to the moist or wet hair. In this latter method the water-free composition of the invention, e.g. a dry shampoo, includes gasified particles or contains gasified particles that contain a gas enclosed in a solid aqueous enveloping material or matrix. Preferably from 5 to 30 g of the composition according to the invention is distributed on the wet or moistened hair according to the abundance of the hair. This portion of the composition according to the invention preferably contains from 0.5 to 6 g, especially preferably 1 to 3 g, or is 10 to 20 percent by weight of the gasified particles. Subsequently the hair is combed thoroughly, put in a hairstyle and dried.

It has been found that the above-described gasified particles can also be used for preparation of an instant gel preparation. The present invention also includes this instant gel preparation. The instant gel preparation according to the invention also includes a mixture of dry substances comprising (A) at least one gel-former; and (B) at least one solid material that produces a detectable acoustic effect on contact with moisture.

Substances (B) that produce the acoustic effect are the above-described gasified particles, which contain a gas enclosed in a solid enveloping material or matrix. The envelope or matrix is selected so that the gas is released on contact of the enveloping material with water or moisture. The pressure of the gas enclosed in the particles is preferably greater than the surrounding pressure.

The gel-formers (A) are principally all those viscosity increasing or gelatinizing easily water-soluble materials that do not clump or easily water-swelling materials, e.g. starches and starch derivatives, which are conventionally used in the known instant products.

Super-absorbing polymers are preferred gel-formers. Polyacrylates or polymethacrylates, especially their sodium salts, which have a high molecular weight (MW e.g. >1,000,000) and are cross-linked are super-absorbing polymers. They take up many times their own weight on contact with water and form gelatinized particles. The super-absorbing polymers form swelling gelling particles, which are present in dispersed or associated form in the ready-to-use gel, on contact with water or an aqueous solution. Super-absorbing polymers are known from their use as absorbers for liquids, especially absorbing sanitary articles, such as baby diapers, and in incontinence training, feminine hygiene and wound coverings. They can be defined as water-soluble cross-linked polymers, which are in a position to take up a multiple, i.e. up to 1000 times, its own weight, of an aqueous liquid by swelling and forming a hydro gel and give back or release the absorbed liquid under pressure. These super-absorbing polymers include polymers or hydrophilic copolymers of acrylic or methacrylic acid or graft copolymers made from starches and acrylic acid, in which the polymers can be present in neutralized or partially neutralized form as salts and typically have high molecular weight (e.g. MW >1,000,000). They are formed by polymerization with partial cross-linking with suitable cross-linking agents selected from the group consisting of ethylenic unsaturated hydrophilic monomers, especially acrylic acids, methacrylic acids or their alkali salts. These polymers are well known and their production has been described many times, for example see EP 0 312 952, DE 44 18 818 and EP 0 441 507. The super-absorbing polymers are characterized by their great water absorptivity and their water-retention ability. They are obtained commercially in the form of a powder or granulate. Suitable super-absorbing polymers include, for example, AQUA-KEEP® D (Elf Atochem S.A.), Sanwet® IM 7015 (BASF AG) or Sanwet® 3746-5 (BASF AG). The average particle size of the dried polymers amounts to preferably 100 to 850 μm. Generally smaller particle sizes of 200 μm or less are especially preferable. The water up-take for desalinated water (centrifuge retention capacity) is preferably at least 20 g/g.

The gel-formers (A) preferably are included in the ready-to-use or ready-to-apply gel in an amount of from 0.05 to 20 percent by weight, especially preferably from 0.1 to 2 percent by weight, and even more preferably from 0.3 to 1 percent by weight. They preferably provide the gel formers for the individual commercially ready-to-apply gel. The materials (B) producing the detectable acoustic effect are preferably contained in the ready-to-use or ready-to-apply gel in an amount of from 0.1 to 20 percent by weight, especially preferably from 0.5 to 10 percent by weight and even more preferably from 1 to 2 percent by weight.

The ratio of the amount of gel-former (A) and material (B) producing the acoustic effect is selected according to the gel-forming speed of the gel former so that the production of the acoustic effect after addition of water or a water-containing solvent ends at the time point, at which the preparation has achieved a ready-to-apply consistency, i.e. when the composition is essentially completely gelled and its viscosity does not substantially change further or remains unchanged. This time point preferably occurs at from 1 to 60 minutes, preferably at 1 to 15 minutes, after contact of the dry instant gel preparation with water or with an aqueous solvent. Suitable amount ratios are in a range of gel former (A) to material (B) for producing the acoustic effect of from 1:0.5 to 1:20, preferably from 1:1 to 1:10.

The instant gel preparation according to the invention is usable, for example, for making cosmetic, pharmaceutical or medicinal composition or foods. The subject matter of the invention thus also includes a cosmetic composition with an acoustic indicator, which contains the preparation according to the invention or comprises that preparation. The cosmetic composition according to the invention preferably contains additional additive or effective ingredients in solid form as a powder or granulate, which is easily and dissolved or uniformly dispersed with stirring in water. These additional additive or effective ingredients include e.g. solid detergents, detergent mixtures, dye compounds, micro-encapsulated perfume, aroma or care providing compositions. These additional auxiliary and active ingredients can be used in amounts of from 0.01 to 5 percent by weight.

Additional auxiliary and adjuvant substances, which are used in liquid form, e.g. perfume oils, are preferably provided in micro-encapsulated form. The micro-capsules of the added substance, especially of perfume oil, are provided in a known manner, see literature, e.g. Soap-oils-fats-waxes, 115, Nr. 3, pp. 93–98 (1989). The capsule material can be provided so that it is sufficiently stable in an aqueous medium and the capsule contents are released by mechanical action, e.g. by rubbing with the hands. The capsule material can however also be provided so that it dissolves and the contents of the capsule are released partially or completely in the ready-to-use gel within 1 to 60 minutes, preferably 1 to 15 minutes. The material (B) producing the detectable acoustic effect could thus also be used as an acoustic indicator to determine whether or not a sufficient release of the auxiliary and active ingredients of an initially water-free preparation including them has occurred. The auxiliary and active ingredients would be present in the preparation initially in micro-capsules made of a material that is unstable in aqueous media. Cyclodextrin is a suitable soluble capsule material. The diameter of the microcapsules amounts to preferably from 5 to 2000 $\mu$m, preferably from 75 to 250 $\mu$m.

Suitable powdery surfactant compounds, e.g. for making a cleansing composition according to the invention, are disclosed in DE 197 45 964. Suitable anionic detergents include sulfonated or sulfated alkyl-, aralkyl- or alkylaryl detergents, alkyl ether sulfates, alkyl ether sulfonates, alkyl succinates, alkyl sulfosuccinates, alkyl ester sulfonates, N-alkoylsarcosinates, methyltaurates, taurates and isethionates, in so far as they are in solid form and have a sufficient water solubility. Sodium, magnesium, ammonium and mono-, di- or triethanol amine salts of alkyl or aryl sulfonates, in which the alkyl groups have generally 12 to 21 carbon atoms and can be unsaturated or preferably saturated, are especially preferred. Mono-quaternary or bis-quaternary ammonium compounds, which have at least one long chain aliphatic group with 10 to 26 carbon atoms, can be used as cationic detergent compounds. Condensation products of ethylene oxide or propylene oxide with long-chain alcohols, long-chain amines or long-chain carboxylic acids can be used as non-ionic detergents, in so far as they are not liquid and sufficiently water-soluble. The carbon chains of the long-chain compounds usually include from 8 to 20 carbon atoms and can be condensed with at least two, preferably from 5 to 20 ethylene oxide or propylene oxide units. Also alkylpolyglycosides with eight to fourteen carbon atoms in their alkyl chain, such as lauryl polyglucose, can be used as the nonionic detergents. All betaines, which have a long-chain alkyl group can be used as the amphoteric or zwitterionic detergents. These betaines include alkylamidopropylbetaines, alkylbetaines, alkylamphoacetates and -diacetates, sulfobetaines and phosphobetaines, which have alkyl groups containing 8 to 20 carbon atoms, in as much as they are in solid form and have sufficient water solubility. Coconut dimethylcarboxymethylbetaine, lauryldimethylcarboxylmethylbetaine, lauryldimethylcarboxyl-$\alpha$-methylbetaine and cetyldimethylcarboxymethylbetaine, also sulfobetaines, such as coconut diemthylsulfodimethylbetaine, amidoalkylbetaine and amidoalkylsulfobetaine, are especially suitable. The carboxybetaines and amidobetaines are especially preferred. Coconut amidopropylbetaine, lauramidopropylbetaine, myristylamidopropylbetaine and their mixtures are special examples.

Suitable solid dye compounds, for example, are those which are usually used to dye foods or for cosmetics, e.g. Acid Blue 9 (Food Blue 2, C.I. 42090), Acid Red 51 (Food Red 14, C.I. 45430), Acid Yellow 3 (Food Yellow 13, C.I. 47005) or Acid Green 25 (C.I. 61570).

Because the sugar envelope for the gasified particles itself has a high affinity for hair, a positive volume or styling effect for the treated hair can be created by treatment of the hair with the cosmetic compositions according to the invention. For increasing the fixing effect additional solid rapidly dissolving hair-fixing materials can be added, for example additional saccharides or polysaccharides, e.g. glucose.

The viscosity of the ready-to-use gel amounts to preferably from 500 to 3000 mPa.s, especially preferably from 1000 to 1500 mPa.s (measured with a rotation viscometer, RheoStress 100 of Haake at a temperature of 25° C. and a Schergradient of 0.5 to 1400$s^{-1}$).

The use of the instant gel preparation or the cosmetic composition according to the invention occurs, when either water or a water-containing solvent system is present and the instant gel preparation according to the invention is added or the cosmetic composition containing the instant gel preparation is present and is mixed with water or a water-containing solvent. Subsequently the mixtures are stirred until the acoustic effect is finished and/or the composition has reached its ready-to-use consistency. After that the thickened or gelled product can be provided for its predetermined application.

In a particularly preferred embodiment the instant gel preparation according to the invention contains a superabsorbent polymer and gasified particles, which comprise a solid envelope or enveloping material based on saccharides and carbon dioxide enclosed in that envelope. Additional additive, auxiliary or effective ingredients can be contained in solid, powdery, granulated or micro-encapsulated form.

The following examples illustrated the subject matter of the invention in more detail.

EXAMPLES

In the following examples the product "Popping Candy Nature Dust" of Zeta Espacial S. A., Rubi, Spain, is utilized. This product has gasified particles, which contain from 0.3 to 2.0 ml carbon dioxide per gram in a enveloping material or matrix of sugar, lactose and glucose and have a size of from about 0.5 to 4.5 mm.

Example 1
Hair Balm

- 6.00 g glycerylstearate/polyethyleneglycol-(20)-cetearyl ether
- 4.00 g diquaternary polydimethylsiloxane (Abil® Quat 3272, Goldschmidt AG/Germany)
- 2.00 g cetyl alcohol
- 1.36 g citric acid
- 0.14 g 1,2-dibromo-2,4-dicyanobutane
- 0.12 g perfume
- to 100 g water About 15 g of this material are mixed with 2 to 3 g popping candy prior to application.

Example 2
Hair Rinse

- 4.00 g cetyl stearyl alcohol
- 1.36 g DL-2-pyrrolidon-5-carboxylic acid
- 0.75 g cetyltrimethylammonium chloride
- 0.50 g perfume
- 0.20 g plant extract Extrapon® 5 Special of Dragoco, Germany
- to 100 g water About 15 g of this material are mixed with 2 to 3 g popping candy prior to application.

Example 3
Hair Fixing Composition

- 3.00 g vinylpyrrolidone/vinyl acetate copolymer
- 0.90 g formic acid
- 0.20 g 1,2-propylene glycol
- 0.15 g perfume
- 0.03 g cetyltrimethylammonium chloride
- 20.20 g water
- to 100 g ethanol About 20 ml of this material are mixed with 2 to 3 g popping candy prior to application.

Example 4
Hair Dyeing-Fixing Composition

- 2.50 g vinylacetate/crotonic acid/polyglycol copolymer
- 0.20 g perfume
- 0.07 g 1-amino-4-(2',3'-dehydroxypropyl)amino-5-chloro-2-nitrobenzene
- 0.05 g Basic Brown 17 (C.I. 12 251)
- 0.01 Basic Blue 7 (C.I. 42 595)
- 0.0023 g Basic Violet 14 (C.I. 42 510)
- 50.0 g ethanol
- to 100 g water About 10 to 15% popping candy was added prior to use.

Example 5
Hair Fixing and Styling Composition

- 2.50 g polyvinylpyrrolidone
- 2.00 g hydroxypropyl guar
- 0.80 g hydrogenated castor oil, ethoxylated with 45 Mol ethylene oxide
- 0.60 g DL-2-pyrrolidone-5-carboxylic acid
- 0.45 g sodium benzoate
- 0.30 g hydroxyethylcellulose
- 0.20 g perfume
- 0.09 g sodium formate
- 0.05 g mica/titanium oxide/zinc oxide powder (Soloron® Silver Sparkle, Merck AG, Germany)
- to 100 g water About 10 to 15 g of this material are mixed with 2 to 3 g popping candy prior to application.

Example 6
Hair and Body Shampoo Composition

- 40.00 g lauryl alcohol diglycol ether sulfate sodium salt
- 4.00 g sodium chloride
- 0.05 g dye compound
- 55.85 g water
- 0.10 g preservative agent Immediately prior to use about 10 to 20% popping candy is added to the amount of shampoo to be applied.

Example 7
Permanent Shaping Composition

- 8.0 g thioglycolic acid
- 2.6 g ammonium hydrogen carbonate
- 0.3 g glycerol polyethylene glycol-(35)-ricinoleate
- 0.3 g perfume
- 0.1 g octylphenol, ethoxylated with 20 Mol ethylene oxide to 100 g 20 ml of the composition are immediately mixed with 2 g of popping candy prior to use and applied to the hair.

Example 8
Permanent Shaping Fixing Composition

- 10.0 g sodium bromate
- 3.2 g disodium hydrogen phosphate dodecahydrate
- 0.8 g ortho-phosphoric acid (85 percent)
- 0.5 g monosodium phosphate
- to 100 g water 30 ml of the composition are immediately mixed with 3 g of popping candy prior to use and applied to the hair.

Example 9
Foam Fixing Composition

- 14.0 g hydrogen peroxide (35 percent)
- 3.41 g o-phosphoric acid (85 percent)
- 1.25 g DL-2-pyrrolidon-5-carboxylic acid
- 0.66 g laurylaminodimethyl acetobetaine
- 0.50 g polypropylen-(1)-polyethylen-(9)-laurylglycol ether
- 0.20 g perfume
- 0.05 g p-acetaminophenol
- to 100 g water 15 ml of the composition are immediately mixed with 2 g of popping candy prior to use and applied to the hair.

Example 10
Refreshing Gel
  Instant Gel Preparation:
  0.5 g Sanwet® 3746-5 (BASF, Super-absorbing sodium polyacrylate)
  1.5 g popping candy
  0.1 g micro-encapsulated perfume The instant gel preparation is mixed with stirring in a quantity of water such that the total amount of the preparation equals 100 g. A ready-to-use gel is formed after about 2 to 3 minutes.

Example 11
Gel with Hair Fixing Action
  Instant Gel preparation:
  0.7 g Sanwet® 3746-5 (BASF, Super-absorbing sodium polyacrylate)
  2.0 g popping candy
  0.1 g micro-encapsulated perfume
  2.5 g C-PUR® 1934 (Glucose)

The instant gel preparation is mixed with stirring in a quantity of water such that the total amount of the preparation equals 100 g. A ready-to-use gel is formed after about 2 to 3 minutes.

Example 12
Two-Phase Hair Luster-Giving Gel
  Instant Gel Preparation (Phase 1):
  0.5 g Sanwet® 3746-5 (BASF, Super-absorbing sodium polyacrylate)
  1.0 g popping candy
  0.1 g micro-encapsulated perfume
  Phase 2:
  5.0 g glycerol
  93.4 g water The instant gel preparation (Phase 1) is added to Phase 2 and stirred. It forms a ready-to-apply gel after a swelling time of 2 to 3 minutes.

While the invention has been illustrated and described as embodied in a method of performing cosmetic treatments with gasified solid particles and instant gel preparations containing the gasified solid particles, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. A cosmetic composition comprising a plurality of gasified particles, said gasified particles containing at least one gas enclosed in a solid enveloping material, wherein said solid enveloping material is selected so that said at least one gas is released when said solid enveloping material comes into contact with water or moisture.

2. The cosmetic composition as defined in claim 1 and consisting of a first preparation and a second preparation separate from said first preparation, said first preparation containing at least one cosmetic active ingredient in an aqueous foundation and said second preparation being water-free and comprising said gasified particles or said gasified particles in a water-free base.

3. The cosmetic composition as defined in claim 1 and consisting of a substantially water-free single preparation.

4. The cosmetic composition as defined in claim 3, in the form of a dry shampoo and containing at least one detergent or detergent mixture.

5. An instant gel preparation comprising a mixture of dry ingredients, said mixture containing at least one gel former and gasified particles for producing a detectable acoustic effect when said mixture comes into contact with water or moisture, said gasified particles containing at least one gas enclosed in a solid enveloping material, wherein said at least one gel former and said gasified particles for producing a detectable acoustic effect are present in a predetermined ratio such that said acoustic effect produced after addition of said water or moisture or after addition of a water-containing solvent system is ended at a time point at which gelling is essentially complete.

6. The preparation as defined in claim 5, wherein said solid enveloping material is selected from the group consisting of sacchrides and sugar materials derived therefrom that release said at least one gas from said enveloping material on contact with said water or moisture; said at least one gas is selected from the group consisting of carbon dioxide, nitrogen and air and said at least one gas contained in said gasified particles has a pressure greater than a surrounding pressure acting on said gasified particles.

7. The preparation as defined in claim 5 or 6, wherein said at least one gel former is selected from the group consisting of super-absorbing polymers and starches.

8. The preparation as defined in claim 5, wherein said predetermined ratio of said at least one gel former to said gasified particles for producing the detectable acoustic effect is from 1:0.5 to 1:20.

9. A cosmetic composition with an acoustic indicator, wherein said cosmetic composition comprises an instant gel-preparation, said instant gel-preparation comprises a mixture of dry ingredients, said dry ingredients containing at least one gel former and a plurality of gasified particles, said gasified particles containing at least one gas enclosed in a solid enveloping material, said solid enveloping material is selected from the group consisting of saccharides and sugar materials derived from said saccharides that release said at least one gas from said enveloping material on contact with said water or moisture; said at least one gas is at least one member selected from the group consisting of carbon dioxide, nitrogen and air and said at least one gas contained in said gasified particles has a pressure greater than a surrounding pressure acting on said gasified particles, wherein said at least one gel former and said gasified particles for producing a detectable acoustic effect are present in a predetermined ratio such that said acoustic effect produced after addition of said water or moisture, or after addition of a water-containing solvent system, is ended at a time point when gelling is essentially complete.

10. The cosmetic composition as defined in claim 9, wherein said at least one gel former is selected from the group consisting of super-absorbing polymers and starches.

11. The cosmetic composition as defined in claim 9, wherein said predetermined ratio of said at least one gel former to said gasified particles for producing the detectable acoustic effect is from 1:0.5 to 1:20.

12. The cosmetic composition as defined in claim 9, further comprising additive and active ingredients in solid form.

13. The cosmetic composition as defined in claim 9, further comprising an instant gel preparation containing at least one super-absorbing polymer in solid form and said gasified particles, and said at least one gas consists of carbon dioxide enclosed in said solid enveloping material.

14. The cosmetic composition as defined in claim 13, further comprising additive and active ingredients in solid form.

15. A method of treating hair, said method comprising the steps of:
   a) washing, rinsing or otherwise moisturizing the hair with water;
   b) providing a water-free composition comprising gasified particles, said gasified particles containing at least one gas enclosed in a solid enveloping material, wherein said solid enveloping material is selected so that said at least one gas is released on contact of the solid enveloping material with water or moisture; and
   c) applying said water-free composition to the hair after the washing, rinsing or other wise moisturizing of step a).

16. A method of treating hair, said method comprising the steps of:
   a) providing a plurality of gasified particles, said gasified particles containing at least one gas enclosed in a solid enveloping material at a pressure greater than a surrounding pressure, said solid enveloping material being selected so that said at least one gas is released when said solid enveloping material at least partially dissolves when the gasified particles come into contact with water;
   b) mixing a water-containing hair treatment composition with the gasified particles to form a mixture, so that said at least one gas is released and an audible acoustic effect consisting of a popping effect occurs during the release of the at least one gas; and
   c) applying said mixture to the hair immediately after the mixing of step b).

17. The method as defined in claim 15 or 16, wherein said solid enveloping material is selected from the group consisting of saccharides and sugar materials derived from said saccharides; said at least one gas is selected from the group consisting of carbon dioxide, nitrogen and oxygen; said at least one gas enclosed in said solid enveloping material has a pressure greater than a surrounding pressure acting on said gasified particles and an acoustic effect occurs during the contacting of the gasified particles with said water or moisture to release said at least one gas.

18. The method as defined in claim 15 or 16, wherein said solid enveloping material is coated with a coating material.

19. The method as defined in claim 15 or 16, wherein said solid enveloping material is coated with a coating material selected from the group consisting of fats, shellac, gelatin, cellulose and cellulose compounds.

20. The method as defined in claim 15 or 16, wherein from 0.05 to 15 $cm^3$ of said gas per gram of a total amount of said gas particles are enclosed in said enveloping material.

21. A method of making a cosmetic preparation having a predetermined viscosity or thickness, said method comprising the steps of:
   a) providing a dry instant gel-forming preparation comprising a plurality of gasified particles, said gasified particles containing at least one gas enclosed in a solid enveloping material and at a pressure greater than a surrounding pressure, said solid enveloping material being selected so that said at least one gas is released and an audible acoustic effect consisting of a popping effect occurs when said solid enveloping material at least partially dissolves due to contact of the gasified particles with water;
   b) providing another composition comprising water; and
   c) mixing the dry instant gel-forming preparation comprising the gasified particles with said another composition comprising water in a predetermined weight ratio to form said cosmetic preparation, so that said at least one gas is released and said popping effect occurs and so that said popping effect ends when gelling is essentially complete.

22. The method as defined in claim 21, wherein said solid enveloping material is selected from the group consisting of saccharides and sugar materials derived from said saccharides and said at least one gas is selected from the group consisting of carbon dioxide, nitrogen and oxygen.

23. The method as defined in claim 22, wherein said solid enveloping material is coated with a coating material.

24. The method as defined in claim 22, wherein said solid enveloping material is coated with a coating material selected from the group consisting of fats, shellac, gelatin, cellulose and cellulose compounds.

* * * * *